(12) United States Patent
Johnson

(10) Patent No.: US 7,182,853 B2
(45) Date of Patent: Feb. 27, 2007

(54) REDOX CONTROL/MONITORING PLATFORM FOR HIGH THROUGHPUT SCREENING/DRUG DISCOVERY APPLICATIONS

(75) Inventor: Jay Johnson, Dayton, OH (US)

(73) Assignee: University of Dayton, Dayton, OH (US)

( * ) Notice: Subject to any disclaimer, the term of this patent is extended or adjusted under 35 U.S.C. 154(b) by 755 days.

(21) Appl. No.: 09/957,729

(22) Filed: Sep. 21, 2001

(65) Prior Publication Data

US 2002/0123069 A1 Sep. 5, 2002

Related U.S. Application Data

(60) Provisional application No. 60/234,477, filed on Sep. 22, 2000.

(51) Int. Cl.
G01F 1/64 (2006.01)
G01N 27/26 (2006.01)
G01N 33/553 (2006.01)

(52) U.S. Cl. ............ 205/782; 205/775; 205/792; 204/400; 204/403.01; 204/405; 204/412; 204/196.06; 436/524; 436/525; 436/150; 436/172

(58) Field of Classification Search ............ 435/3, 435/286.01, 287.1, 287.3, 288.7; 436/149, 436/150, 164, 172
See application file for complete search history.

(56) References Cited

U.S. PATENT DOCUMENTS

| | | | |
|---|---|---|---|
| 4,318,784 A * | 3/1982 | Higgins et al. ............ 205/452 |
| 4,385,666 A | 5/1983 | Mamadzhanov et al. |
| 4,704,353 A | 11/1987 | Humphries et al. |
| 4,883,579 A | 11/1989 | Humphries et al. |
| 4,963,245 A * | 10/1990 | Weetall ................. 205/777.5 |
| 4,963,815 A | 10/1990 | Hafeman |
| 5,200,051 A * | 4/1993 | Cozzette et al. ....... 204/403.07 |
| 5,538,687 A * | 7/1996 | Kotzan et al. ............... 422/52 |
| 5,567,302 A | 10/1996 | Song et al. |
| 5,858,799 A | 1/1999 | Yee et al. |
| 5,879,949 A | 3/1999 | Cole et al. |
| 5,942,102 A | 8/1999 | Hodges et al. |
| 6,051,380 A * | 4/2000 | Sosnowski et al. ............ 435/6 |
| 6,232,085 B1 | 5/2001 | Pantoliano et al. |
| 6,238,869 B1 | 5/2001 | Kris et al. |
| 6,246,046 B1 | 6/2001 | Landers et al. |
| 6,251,595 B1 | 6/2001 | Gordon et al. |
| 6,277,576 B1 | 8/2001 | Meade et al. |
| 6,281,006 B1 | 8/2001 | Heller et al. |

FOREIGN PATENT DOCUMENTS

| | | |
|---|---|---|
| DE | 198 32 598 | 3/2000 |
| DE | 199 16 921 A | 10/2000 |
| DE | 199 16 921 A1 | 10/2000 |
| DE | 199 17 052 | 10/2000 |
| EP | 1 065 170 A | 1/2001 |
| WO | WO 89 10551 A | 11/1989 |

OTHER PUBLICATIONS

Yu et al., "Variable thickness thin-layer cell for electrochemistry and in situ UV-VIS absorption, luminescence and surface-enhanced Raman spectroelectrochemistry", 97/2000, Analytica Chimica Acta, 420(1):45-55.*
Johnson, Jay M. et al., "Metal Complexes as Mediator-Titrants for Electrochemical Studies of Biological Systems" Analytical Biochemistry 133, 1983, pp. 186-189.
Johnson, Jay M. et al., "Potential-Dependent Enzymatic Activity in an Enzyme Thin-Layer Cell" Anal. Chem. 1982, 54, pp. 1377-1383.
Asanov, Alexander N. et al., "Heteroenergetics of Bovine Serum Albumin Adsorption from Good Solvents Related to Crystallization Conditions" Journal of Colloid and Interface Science 191, Article No. CS974955, 1997, pp. 222-235.
Heineman, William R., spectro-electro-chemistry "Combination of Optical and Electrochemical Techniques for Studies of Redox Chemistry" Analytical Chemistry, vol. 50, No. 3, Mar. 1978, pp. 390A-402A.
Asanov, Alexander N. et al., "Regenerable Biosensor Platform: A Total Internal Reflection Fluorescence Cell with Electrochemical Control" Analytical Chemistry, vol. 70, No. 6, Mar. 15, 1998, pp. 1156-1163.
Rabinowitz, Joshua D. et al., "Potentiometric Measurement of Intracellular Redox Activity" J. Am. Chem. Soc. 1998, 120, pp. 2464-2473.
Heineman, WR, "Studies of biological redox systems by thin-layer electrochemical techniques", Advances in Chemistry Series, vol. 201, 1982, pp. 1-21.

* cited by examiner

Primary Examiner—Peter Paras, Jr.
Assistant Examiner—My-Chau T Tran
(74) Attorney, Agent, or Firm—Dinsmore & Shohl LLP

(57) ABSTRACT

The invention is a redox control and monitoring platform that is to be used in conduction with another detection scheme. The platform includes a portion of an electrochemical control. The electrochemical control can be operated to control and measure the redox environment of a sample. The electrochemical control can be provided in a multiplicity of test regions to allow high throughput analysis of a multiplicity of samples. The present method and system allows the determination of the effect of the change in redox environment on the binding or other activity of the species in the sample that is directly affected by the redox environment.

10 Claims, 3 Drawing Sheets

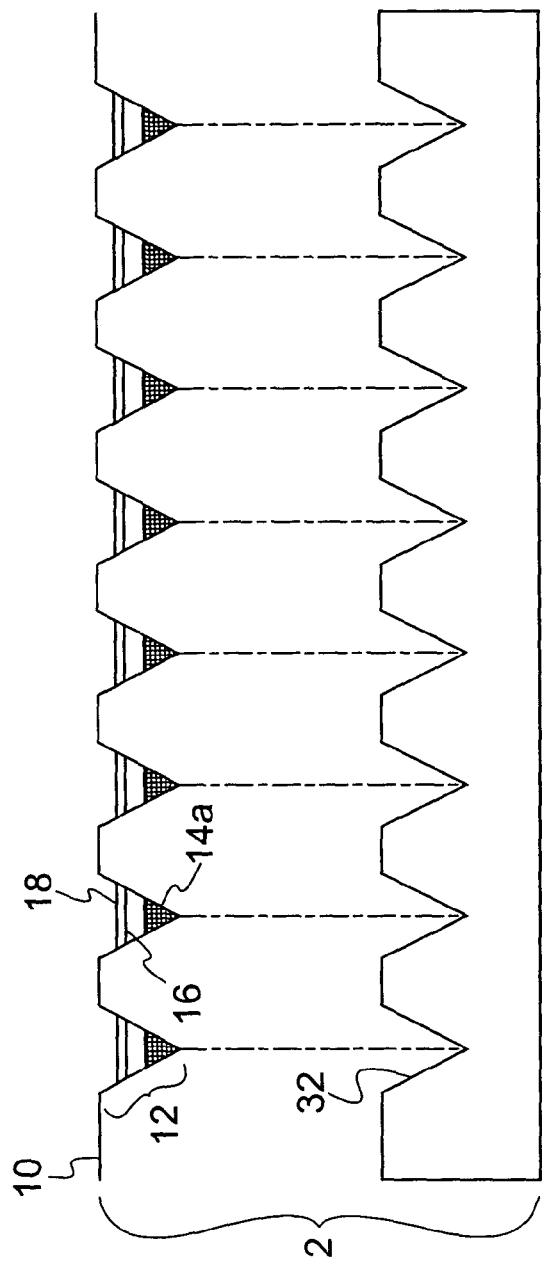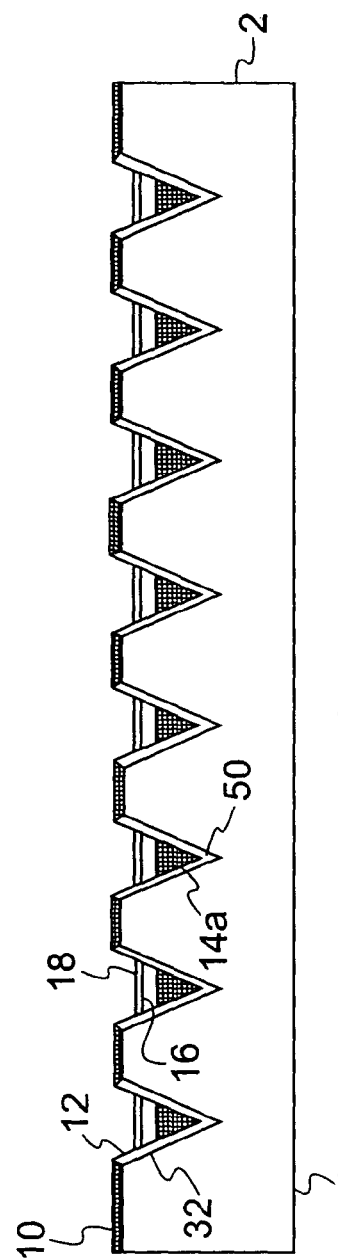

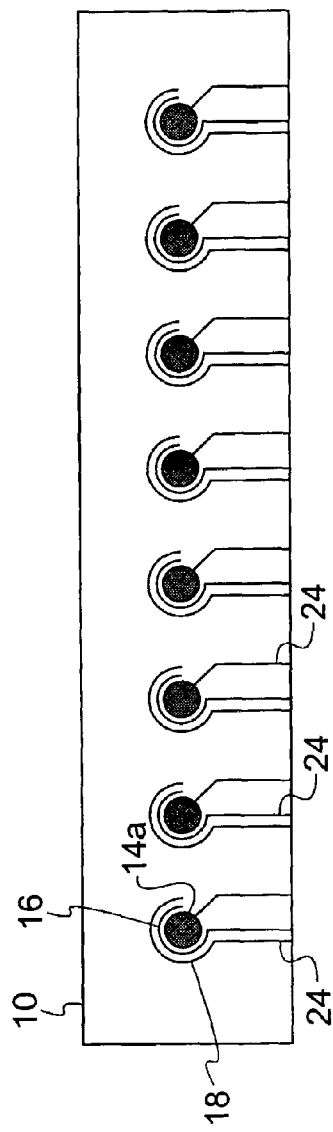
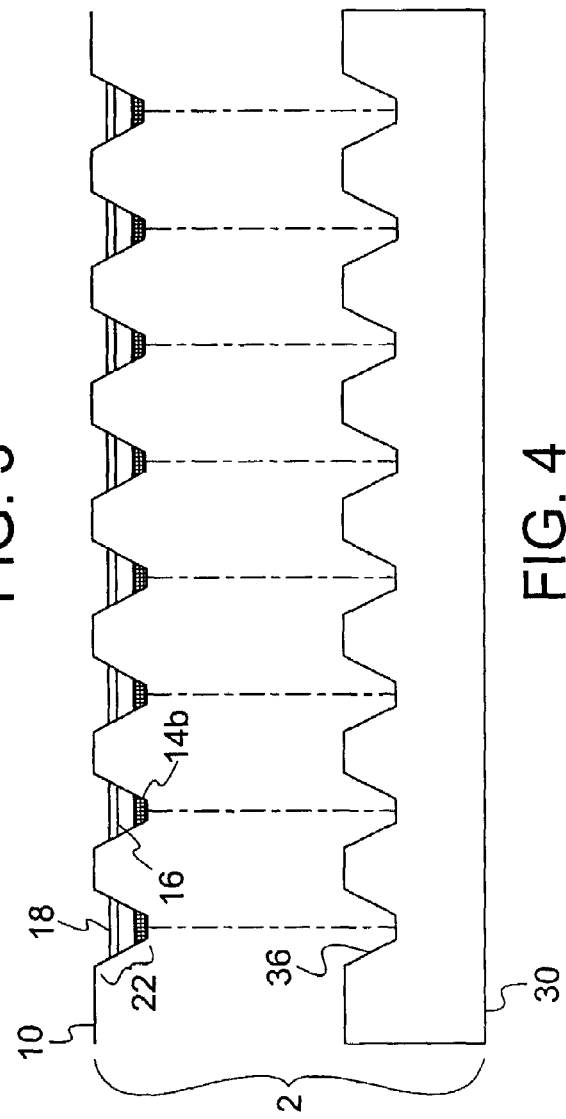
FIG. 3
FIG. 4

REDOX CONTROL/MONITORING PLATFORM FOR HIGH THROUGHPUT SCREENING/DRUG DISCOVERY APPLICATIONS

CROSS-REFERENCE TO RELATED APPLICATIONS

This application claims the benefit of U.S. Provisional Application Ser. No. 60/234,477, filed Sep. 22, 2000.

BACKGROUND OF THE INVENTION

The present invention relates to a redox control and monitoring platform and, more particularly, to a redox control and monitoring platform that is to be used in conjunction with another detector during high throughput screening and drug discovery applications.

A great number of studies have demonstrated the importance of the redox environment in the regulation of a number of cellular functions in both normal and diseased states. Such processes include those that involve redox active proteins and enzymes, free radical damage, and oxidative stress. The redox environment can influence both catalysis and binding affinity. Additionally, transcription of DNA into mRNA, the translation of mRNA into proteins, and the rate of transport of glutamate across the nerve synapses have all been shown to depend on the redox environment. The cellular redox environment has also been implicated in the modulation of more complex cellular events such as proliferation and apotosis, and the specific redox environment can also activate certain drugs. It is apparent that the redox environment of a target molecule or species can have a great affect on the efficacy of a particular drug.

Researchers often use high throughput systems to analyze a large library of compounds that could have a desired activity. An example of a system useful for high throughput screening and assay is shown in U.S. Pat. No. 6,238,869 to Kris, et al, which is hereby incorporated by reference. Such systems allow researchers to quickly test a huge number of compounds and discard those that do not show the desired activity or quality. Such systems are especially useful in the drug discovery process because large scale testing of a series of compounds can be accomplished quickly and relatively cheaply. Only those compounds that show desired activity are tested further. Without high throughput technology, the screening of such a large number of compounds would be virtually impossible.

Current high throughput drug screening discovery processes do not provide for the measurement of the redox environment or the active control of the redox environment of a target. Much of the current high throughput technology relies on spectroscopic, especially fluorescent, methods to provide information about how or if a particular compound is reacting with a target. However, researchers cannot generally make such measurements while actively controlling the redox environment.

Many methods do exist to measure the redox environment. An example of such a system is shown in U.S. Pat. No. 4,963,815 to Hafeman. However, such a system does not provide for active control of the redox environment of the sample. Additionally, the systems do not provide other data other than electrical measurements, such as spectroscopic measurements. The systems also are not adapted for use in a high throughput process.

Electrochemistry and spectroscopy have been combined to perform various studies. Heineman, *Spectro-electrochemistry: Combination of Optical and Electrochemical Techniques for Studies of Redox Chemistry*, Anal. Chem. 1978, 50, 390–402; Asanov et al., *Heteroenergetics of Bovine Serum Albumin Adsorption from Good Solvents Related to Crystallization Conditions*, J. of Colloid and Interface Science 1997, 191, 222–235; Johnson et al., *Potential-Dependent Enzymatic Activity in an Enzyme Thin-Layer Cell*, Anal. Chem 1982, 54, 1377–1383. The thin-layer spectrochemical methods are often used to characterize the fundamentals of electron transfer between and within redox active enzymes and other biomolecules. The change in redox potential changes the ratio of the redox forms of the enzymes that the spectroscopic technique is generally measuring. However, these methods cannot be generally performed under conditions where assays independent of the redox potential can be performed. When independent assays have been performed, they involved immobilized biomolecules on a surface or within a membrane. It is known that this immobilization can alter the biological activity and the nature and extent of their interaction with proteins or other potential binding partners such as drugs. Additionally, these methods are not generally applicable to a wide variety of systems and sample types.

Accordingly, there is a need for a versatile system that can provide measurement and control of the redox environment that is independent of other assays that can be performed on the sample, especially in high throughput screening.

SUMMARY OF THE INVENTION

This need is met by the present invention wherein a system and method for the control and measurement of the redox environment is disclosed. This system can be combined with other existing detection systems to provide information about how a species reacts or interacts with other species under a controlled set of redox conditions. This system and method are especially useful for high throughput analysis and drug discovery.

In accordance with one embodiment of the present invention a method for analyzing a sample is provided. The method comprises providing an electrochemical control for the redox environment of the sample in a test region and providing a detection scheme consisting of at least one of the following: electrochemical, spectroscopic, radioassay, or magnetic field measurement. The test region may be any structure that can hold a sample and allow the detection scheme to be performed such as a beaker, a test tube, a microplate or other reaction chamber. The electrochemical control is operated to measure and control the redox potential of the sample, and the detector is operated to analyze the sample. The electrochemical control preferably has at least two electrodes.

The electrochemical detection scheme can be amperometry, voltammetry, capacitance or impedance. Preferred is a spectroscopic detection scheme such as fluorescence, absorbance, infra red, phosphorescence, chemiluminescence, electroluminescence, Raman, electron spin resonance or refractive index.

In an alternative embodiment, the electrochemical control can be provided in a multiplicity of test regions. The test regions can be the wells of a microplate. For example, a ninety-six well microplate can be used. The electrochemical controls can be operated separately to provide a different redox environment in each of the wells. A different sample can be placed in each of the wells of the microplate, and the electrochemical control and detection scheme can independently control and analyze each of the samples in the microplate wells. The electrodes can be provided in the microplate by mounting the controls on the protrusions of a second plate. The second plate is placed over the microplate so that the protrusions fit into the wells of the microplate. The protrusions may be conical or truncated cones.

This embodiment is particularly suited for high throughput screening. Combinatorial chemistry can be used to generate a large number of chemical compounds targeted to a variety of applications such as drug discovery or superconductive ceramics. High throughput screening is then used to sort through the enormous number of candidates in order to identify those that have the desired property. The assay that is used in the high throughput screening protocol is designed specifically for the application for which the candidate compounds are intended. The electrochemical control can be operated to provide a different redox environment in each well and thus provide additional information about the interaction of the candidates with the target of the sample under specific redox conditions.

In accordance with another embodiment of the present invention a structure is provided for analyzing a sample. The structure consists of a test region, an electrochemical control for the redox environment of the sample and a detection scheme. The detection scheme may be an electrochemical, spectroscopic, radio assay or magnetic field measurement detector. The electrochemical control is a system that has at least two electrodes.

In a preferred embodiment of the invention, the electrochemical control is provided in a multiplicity of test regions. The test regions may be wells in a microplate. The electrochemical control can be separately operated to provide a different redox environment in each well of the mircroplate. The electrodes are provided in the wells of the microplate by mounting them on the protrusions of a second plate. The protrusions fit into the wells of the microplate. This arrangement allows the detector of the detection scheme access to the sample from the bottom of the microplate. The electrodes may be operated prior to and/or during the operation of the detector to allow analysis of the sample under a controlled redox environment.

In another embodiment of the invention a method of high throughput drug screening is provided. The method comprises providing a surface comprising a plurality of test regions, providing an electrochemical control for the redox environment of the test region in each test region, providing a detection scheme that is selected from at least one of the following: electrochemical, spectroscopic, radio assay and magnetic field measurement, adding at least one target molecule or species to each of the test regions, and adding at least one sample containing a drug candidate to be tested to each test region. The electrochemical control is operated separately for each test region. The detector is subsequently operated to identify if interaction has occurred between the target and the sample.

The electrochemical detection scheme can be amperometry, voltammetry, capacitance or impedance. The spectroscopic detection scheme can be a fluorescence, absorbance, infra red, phosphorescence, chemiluminescence, electroluminescence, Raman, electron spin resonance or refractive index.

The test regions may be a multiplicity of wells in a microplate. A portion of electrochemical control may be contained on a plate with protrusions wherein the electrodes are deposited on the protrusions of the plate. The plate is placed over the microplate so that the protrusions of the plate fit into the wells of the microplate. The protrusions may be conical or truncated cones.

In yet another embodiment of the present invention, a method for performing high throughput assays of non-biological samples is provided. The method comprises providing a surface comprising a plurality of test regions, providing an electrochemical control for the redox environment of the test region in each test region, providing a detection method that is selected from at least one of the following: electrochemical, spectroscopic, radio assay and magnetic field measurement, adding at least one target molecule or species to each of the test regions, and adding at least one sample containing a species to be tested to each test region. The electrochemical control can be operated separately for each test region. The detector of the detection scheme is subsequently operated to identify if interaction has occurred between the target and the sample. This method allows the species that shows the desired activity under the selected redox conditions to be more easily identified. This method could be useful when inorganic compounds or polymers are synthesized using combinatorial methods as candidates for a variety of applications including superconductive ceramics or conductive polymers.

Accordingly, it is an object of the present invention to provide an electrochemical control for the redox environment of a sample that is coupled with an independent detection method. A further object of the present invention is to provide a method and system for providing separate control of the redox environment of a multiplicity of samples for increased throughput analysis. Other objects of the present invention will be apparent in light of the description of the invention embodied herein.

BRIEF DESCRIPTION OF THE DRAWINGS

FIG. 1 is a cross-section side view of a portion of the electrochemical control and the test regions showing the top plate and bottom plate separately.

FIG. 2 is cross-section side view of the mated top plate and bottom plate with conical wells.

FIG. 3 is a bottom view of the top plate.

FIG. 4 is a cross-section side view of another embodiment of a portion of the electrochemical control and the test regions showing the top and bottom plate separately.

DETAILED DESCRIPTION OF THE PREFERRED EMBODIMENTS

Figure 5:
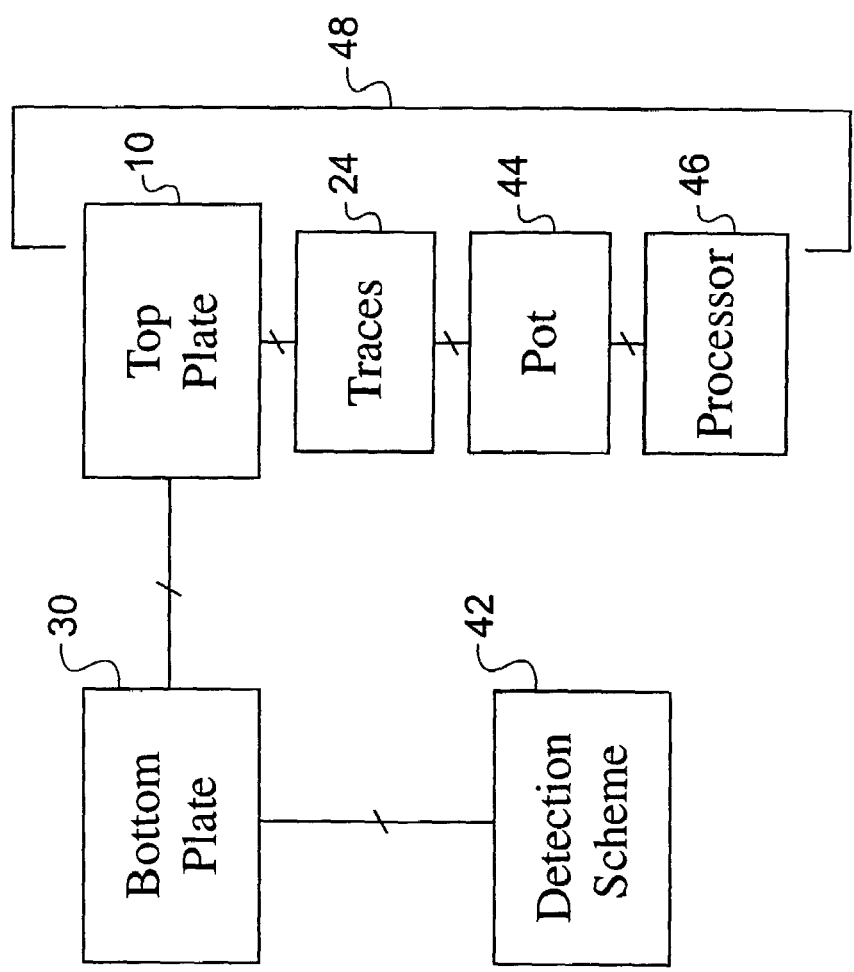
FIG. 5 is a block diagram of the preferred embodiment.

Referring initially to FIGS. 1 and 2, a particular embodiment of the electrochemical control assembly of the present invention is described in detail. A control assembly 2 according to the present invention includes a bottom plate 30 with sample wells 32, a top plate 10 with protrusions 12, and electrodes 14a, 16, 18 disposed on the protrusions 12.

The top plate 10 is configured so that protrusions 12 containing the electrodes 14a, 16, 18 fit into the sample wells 32 of the bottom plate 30 when the top plate 10 is placed over the bottom plate 30. This configuration forms a test region 50. Each of the sample wells 32 can hold a separate sample, and each of the electrode arrangements 14a, 16, 18 on the protrusions 12 can be operated to separately control or measure the redox environment of each of the sample wells 32.

The top plate 10 can be a reusable plate made out of plastic or ceramic. The bottom plate 30 can be made of transparent plastic or another transparent material, and the bottom plate 30 maybe disposable. Referring to FIG. 3, the electrodes 14a, 16, 18 are connected to electrical traces 24.

The electrodes 14a, 16, 18 and electrical traces 24 are applied onto outer conical protrusions 12 of the top plate 10. The electrodes 14a, 16, 18 and traces 24 may be applied by sputtering or vacuum deposition. The electrical traces 24 are extended to the outer edge of the top plate 10 where an electrical connection can be made through an edge connector (not shown).

Referring generally to FIGS. 1, 3 and 5, the traces 24 may be coupled to a multi-channel potentiostat, represented by 44. Each set of electrodes 14a, 16, 18 can be coupled to a separate potentiostat 44 via the traces 24 to allow separate control of the redox environment in each well 32. However, all of the electrodes 14a, 16, 18 could be coupled to a single potentiostat 44 to provide more limited control of the redox environment in each well 32. The potentiostat 44 or potentiostats 44 may be monitored or controlled with a computer or microprocessor 46. The electrochemical control 48 is made up of the electrodes 14a, 16, 18 on the top plate 10, the traces 24, the potentiostat 44 or potentiostats 44 and the processor 46.

Referring to FIGS. 1 and 2, three electrodes 14a, 16, 18 are generally provided on each protrusion 12. The working electrode 14a is the electrode at which the potential is controlled via the potentiostat. The reference electrode 16 is used as a potentiometric probe in order to maintain the potential of the working electrode 14a at a pre-selected value relative to the working electrode 14a. The auxiliary electrode 18 completes the circuit and allows current to flow through the test region 50 contained within the sample well 32. A two electrode system could also be used. In the two electrode system, potential would be controlled via a working electrode. A second electrode, the counter electrode, would serve to complete the circuit and act as a reference electrode. However, a three electrode 14a, 16, 18 system is preferred.

Referring to FIGS. 2 and 4, the sample is first loaded into the wells 32, 36 of the bottom plate 30, and the top plate 10 is installed. The samples are contained in the thin layer 50 formed by the outer protrusions 12, 22 of the top plate 10 and the inner surfaces of the sample wells 32, 36 in the bottom plate 30. The thin layer serves as the test region 50. This arrangement provides a high working electrode surface area to sample volume ratio. The conical shaped protrusions 12 of the embodiment in FIG. 2 prevent bubbles from being trapped in the thin layer 50 after assembly. Rapid equilibration upon changing the potential on the working electrode 14a is achieved because the diffusion path to the electrode is minimized. The top plate 10 could alternatively have protrusions 22 in the shape of a truncated cone 22, as shown in FIG. 4. This could enhance the optical properties of the wells 36 and, thus, provide better excitation and detection.

Mediator titrants are provided in each of the sample wells 32, 36 when the sample includes a larger molecule. Mediator titrants are relatively small redox active compounds that are used to shuttle electrons between larger molecules and the electrode. Larger molecules, including many biocomponents, cannot directly exchange electrons at the surface of the electrode because of their size. Thus, mediator titrants are used to couple the electrode potential 14a to the solution potential and serve as an electrochemically generated redox titrant to reduce and oxidize the large molecules.

The mediator titrants useful in the present invention include, but are not limited to: (1) organic molecules such as 4,4'-bipyridine, menadione, menadiol and 4-mercaptopyridine; (2) macrocyles and chelating ligands of transition metals; (3) ferrocene, ferricinium, hydroquinones, quinines; (4) reducible and oxidizable components of organic salts; (5) cobaltcenes and the hexa- and octacyanides of molybdenum, tungsten, and iron; and (6) the trisbypyridyl and hexamine complexes of transition metals.

Referring to FIGS. 2 and 5, the bottom plate 30 is mounted on a fixture such that the wells 32 in the bottom plate 30 are in alignment with a detection scheme 42. The detection scheme could be a series of optical sources and detectors that are mounted below the bottom plate 30. Optical excitation can thus be applied and emission can be measured using this assembly 2 in conjunction with independent redox control provided by the electrochemical control 48 within the sample wells 32. An example of a suitable optical source and detector is contained in U.S. Pat. No. 6,246,046, which is hereby incorporated by references, and which discloses a method and apparatus for providing an excitation source and detector on one side of a micro target.

The method and system of the present invention do not generally involve the immobilization of biomolecules on the surface of the wells 32, 36 or protrusions 12, 22 because this is a bulk solution method. This is advantageous because it is known that immobilization of biocomponents can alter their biological activity and the nature and extent of their interaction with proteins or other binding partners such as drugs. Additionally, there should be no interference from surface activity or interactions. The present invention avoids these problems associated with immobilizing the biomolecule on the surface of the wells and, thus, presents a more accurate picture of how a particular target reacts.

Additionally, the method and system of the present invention allow an assay of the sample that is only indirectly dependent on the change in redox environment. The present method allows the determination of the effect of the change in redox environment on the binding or other activity of the species that is directly affected by the redox environment. Other methods that utilize redox control and some form of detection are generally measuring a change that is directly dependent on the redox environment. The present invention provides an independent assay that can occur simultaneously with active redox control.

FIGS. 1–4 show an eight well 32, 36 and protrusion 12, 22 assembly 2. Each assembly 2 could have an increased number of wells 32, 36 and protrusions 12, 22. For example, a ninety-six well bottom plate is one preferred size because it is currently the standard size for high throughput assay systems. The well 32, 36 size can be varied so that a larger number of wells 32, 36 can fit onto a plate 30 of the same size. A bottom plate 30 with a large number of wells 32, 36 increases the throughput of the analysis and results in savings in time and resources.

It will be obvious to those skilled in the art that various changes may be made without departing from the scope of the invention which is not to be considered limited to what is described in the specification.

What is claimed is:

1. A method of performing an analysis of a sample comprising:
   providing a sample in a test region;
   providing a target in the test region;
   providing an electrochemical control for the redox environment of the sample;
      wherein the electrochemical control is provided to control each of a multiplicity of test regions, and
      wherein the test regions are each of a multiplicity of wells in a microplate, and
      wherein the electrochemical control may be operated to separately control the redox environment of each well in a microplate, and wherein the electrochemical control has at least two electrodes contained on a plate with protrusions wherein the electrodes are deposited on the protrusions of the plate and the plate is placed over the microplate so that the protrusions of the plate fit into the wells of the microplate, and wherein the protrusions are cone shaped;

operating the electrochemical control to control the redox environment of the sample; and analyzing the sample using a detection scheme, wherein the detection scheme is operated to identify if interaction has occurred between the target and the sample, whereby activity of the sample under redox conditions can be identified.

2. The method as claimed in claim 1 wherein the electrochemical control has three electrodes wherein the first electrode is an auxiliary electrode, the second electrode is a reference electrode, and the third electrode is a working electrode.

3. The method as claimed in claim 1 wherein a mediator titrant is added to the sample.

4. The method as claimed in claim 1 wherein the electrochemical control is operated to control the redox environment and the detection scheme is operated subsequently or simultaneously to detect changes in activity or binding in the sample.

5. The method as claimed in claim 1 wherein the detection scheme comprises an electrochemical detection scheme.

6. The method as claimed in claim 5 wherein the electrochemical detection scheme comprises amperometry, voltammetry, capacitance, or impedance.

7. The method as claimed in claim 1 wherein the detection scheme comprises a spectroscopic detection scheme.

8. The method as claimed in claim 7 wherein the spectroscopic detection scheme comprises fluorescence, absorbance, infra red, phosphorescence, chemiluminescence, electroluminescence, Raman, electron spin resonance, or refractive index.

9. The method as claimed in claim 1 wherein the detection scheme is selected from at least one of the following:

electrochemical;

spectroscopic;

radioassay; or magnetic field measurement.

10. The method as claimed in claim 1 wherein the sample is not immobilized in the test region.

* * * * *